(12) United States Patent
Kramer

(10) Patent No.: US 9,284,447 B2
(45) Date of Patent: Mar. 15, 2016

(54) SILANE/UREA COMPOUND AS A HEAT-ACTIVATED CURING AGENT FOR EPOXIDE RESIN COMPOSITIONS

(71) Applicant: SIKA TECHNOLOGY AG, Baar (CH)

(72) Inventor: Andreas Kramer, Zurich (CH)

(73) Assignee: SIKA TECHNOLOGY AG, Baar (CH)

( * ) Notice: Subject to any disclaimer, the term of this patent is extended or adjusted under 35 U.S.C. 154(b) by 170 days.

(21) Appl. No.: 14/246,768

(22) Filed: Apr. 7, 2014

(65) Prior Publication Data

US 2014/0216655 A1 Aug. 7, 2014

Related U.S. Application Data

(62) Division of application No. 13/061,217, filed as application No. PCT/EP2009/061027 on Aug. 27, 2009, now Pat. No. 8,728,271.

(30) Foreign Application Priority Data

Aug. 27, 2008 (EP) .................................... 08163060

(51) Int. Cl.
*C08L 63/00* (2006.01)
*C08L 75/00* (2006.01)
*C07F 7/18* (2006.01)
*C08K 3/36* (2006.01)
*C09J 163/00* (2006.01)

(52) U.S. Cl.
CPC ............... *C08L 63/00* (2013.01); *C07F 7/1836* (2013.01); *C08K 3/36* (2013.01); *C08L 75/00* (2013.01); *C09J 163/00* (2013.01)

(58) Field of Classification Search
CPC ............. C08L 3/00; C08L 3/36; C08L 75/00; C09J 163/00; C08K 3/36
USPC ........................................................ 156/330
See application file for complete search history.

(56) References Cited

U.S. PATENT DOCUMENTS

| | | |
|---|---|---|
| 3,754,971 A | 8/1973 | Pepe et al. |
| 5,073,601 A | 12/1991 | Mülhaupt et al. |
| 5,707,439 A | 1/1998 | Takekoshi et al. |
| 6,197,849 B1 | 3/2001 | Zilg et al. |
| 6,322,890 B1 | 11/2001 | Barron et al. |
| 2002/0007003 A1 | 1/2002 | Merz et al. |
| 2003/0159773 A1 | 8/2003 | Tomiyama et al. |
| 2007/0175579 A1 | 8/2007 | Otani et al. |
| 2008/0076886 A1 | 3/2008 | Burns et al. |
| 2009/0075096 A1 | 3/2009 | Butikofer et al. |

FOREIGN PATENT DOCUMENTS

| | | |
|---|---|---|
| DE | 2 123 033 | 8/1972 |
| EP | 0 308 664 A1 | 3/1989 |
| EP | 0 338 985 A2 | 10/1989 |
| EP | 0 353 190 A2 | 1/1990 |
| EP | 1 717 240 A1 | 11/2006 |
| EP | 1 728 825 A1 | 12/2006 |
| JP | B2-3664831 | 6/2005 |
| WO | WO 95/00259 A2 | 1/1995 |
| WO | WO 00/20483 A2 | 4/2000 |
| WO | WO 01/94492 A1 | 12/2001 |
| WO | WO 03/078163 A1 | 9/2003 |
| WO | WO 2004/055092 A1 | 7/2004 |
| WO | WO 2004/106402 A2 | 12/2004 |
| WO | WO 2005/007720 A1 | 1/2005 |
| WO | WO 2005/007766 A1 | 1/2005 |
| WO | WO 2006/052726 A1 | 5/2006 |
| WO | WO 2006/052729 A1 | 5/2006 |
| WO | WO 2007/020266 A1 | 2/2007 |
| WO | WO 2007/025007 A1 | 3/2007 |
| WO | WO 2008/016889 A1 | 2/2008 |
| WO | WO 2008/049857 A1 | 5/2008 |
| WO | WO 2008/049858 A1 | 5/2008 |
| WO | WO 2008/049859 A1 | 5/2008 |
| WO | WO 2008/049860 A1 | 5/2008 |

OTHER PUBLICATIONS

Mel'Nik et al.; "Polysiloxane Xerogels Containing Arch-fixed Urea Groups;" *Russian Journal of Applied Chemistry*; 2006; pp. 981-986; vol. 79, No. 6.
Mel'Nik et al.; "Synthesis of Alkoxysilanes as Starting Substances for Preparation of New Materials by the Sol-Gel Procedure. Silanes with Urea Functional Group;" *Russian Journal of General Chemistry*; 2004; pp. 1658-1664; vol. 74, No. 11.
Hermel-Davidock et al.; "Control of the Block Copolymer Morphology in Templated Epoxy Thermosets;" *Journal of Polymer Science: Part B: Polymer Physics*; 2007; vol. 45.
International Search Report dated Nov. 17, 2009 from International Application No. PCT/EP2009/061027 (with English-language translation).
International Preliminary Report on Patentability dated Mar. 10, 2011 from International Application No. PCT/EP2009/061027 (with English-language translation).
Notification of the Second Office Action dated Oct. 15, 2013 from Chinese Patent Application No. 200980133077.3 (with English-language translation).

*Primary Examiner* — Daniel Lee
(74) *Attorney, Agent, or Firm* — Oliff PLC

(57) ABSTRACT

Silanes of formula (I):

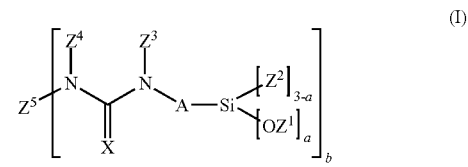

or inorganic fillers whose surface is coated or derivatized with a silane of formula (I), are curing agents for epoxy resins that are activatable at elevated temperature. The thermosetting epoxy resin compositions allow a large reduction in the curing temperature without great impairment of their storage stability. They are therefore very well suited for single-component thermosetting epoxy adhesives, which in particular may contain impact modifiers.

12 Claims, No Drawings

SILANE/UREA COMPOUND AS A HEAT-ACTIVATED CURING AGENT FOR EPOXIDE RESIN COMPOSITIONS

The present application is a divisional application of U.S. patent application Ser. No. 13/061,217 filed on Feb. 28, 2011, which is a U.S. national phase application of International Application No. PCT/EP2009/061027 filed Aug. 27, 2009, and claims the benefit of European Patent Application No. 08163060.0 filed Aug. 27, 2008. The disclosure of each of the prior applications is hereby incorporated by reference herein in its entirety.

TECHNICAL FIELD

The invention relates to the field of silanes and curing agents for thermosetting epoxy resins.

PRIOR ART

Silanes have been known for quite some time as bonding agents for adhesives.

Urea silanes are used for producing sol gels and xerogels, as disclosed in Russ. J. Appl. Chem. 2006, 79, 981-986 and Russ. J. Gen. Chem. 2004, 74, 1658-1664. The urea silanes are condensed with tetraethoxysilane to produce a uniform sol or gel.

Thermosetting epoxy resin compositions have been known for quite some time. For this purpose curing agents are used which are activated at elevated temperature. Urea compounds are an important class of such heat-activatable curing agents for epoxy resins. Such urea compounds often have an accelerating effect on other heat-activatable curing agents containing epoxy resins.

One important application of thermosetting epoxy resin compositions is found in vehicle manufacture, in particular for adhesive bonding or for foaming of cavities in body shells. In both cases, after application of the epoxy resin composition the body is heated in a cathodic dip coating (CDC) oven, thereby also curing and optionally foaming the thermosetting epoxy resin composition. For example, WO 2004/106402 A2 and WO 2004/055092 A1 disclose thermosetting epoxy resin compositions containing urea compounds as heat-activatable curing agents.

However, efforts are currently underway in the industry to greatly reduce the curing temperature. Thus, there is a great need in the industry for thermosetting epoxy resin compositions which also cure at lower temperatures, i.e., at temperatures less than 180° C., after a very short time, typically 10 to 15 minutes. For this reason, aromatic ureas are used which are significantly more reactive due to their structure. However, it has been shown that using such aromatic ureas results in considerable problems in the storage stability of the thermosetting epoxy resin compositions.

DESCRIPTION OF THE INVENTION

The object of the present invention, therefore, is to provide heat-activatable curing agents for epoxy resins, which allow curing of epoxy resins at lower temperatures and still ensure good storage stability of the epoxy resin composition containing these heat-activatable curing agents.

This object has surprisingly been achieved by using a silane of formula (I) according to claim 1.

Such silanes are extremely well suited as heat-activatable curing agents for epoxy resin compositions. In addition, they may be satisfactorily used for the coating or derivatization of substrates, in particular fillers or flat substrates, which may then be used as heat-activatable curing agents.

The silanes of formula (I), in particular formula (I a), are characterized in that, as a component of thermosetting epoxy resin compositions, they allow a large reduction in the curing temperature without great impairment of their storage stability. They are therefore very well suited for single-component thermosetting epoxy adhesives, which in particular contain impact modifiers, as body shell adhesives for vehicle manufacture. It has been shown to be particularly advantageous to use the silanes of formula (I) with further heat-activatable curing agents.

It has also been shown that the silanes of formula (I) result in increased adhesion to various subsurfaces.

Further aspects of the invention are the subject matter of the further independent claims. Particularly preferred embodiments of the invention are the subject matter of the dependent claims.

APPROACHES FOR CARRYING OUT THE INVENTION

In a first aspect, the present invention relates to the use of a silane of formula (I), or of a substrate whose surface is coated or derivatized with a silane of formula (I), as a curing agent for epoxy resins which is activatable at elevated temperature.

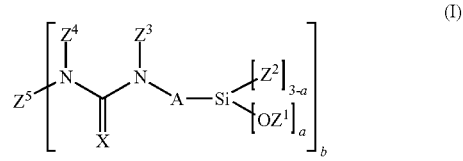

In this regard, A stands for an optionally branched alkylene group containing 1 to 4 C atoms, or for a phenylene group.

$Z^1$ stands for H or an alkyl group containing 1 to 4 C atoms, in particular a methyl or ethyl group.

$Z^2$ stands for H or a phenyl group, or an alkyl group containing 1 to 8 C atoms, in particular a methyl group.

$Z^3$ stands for H or a monofunctional aromatic or cycloaliphatic or aliphatic group containing 1 to 8 C atoms, which optionally contains at least one carboxylate, nitrile, nitro, phosphonate, or sulfonic or sulfonate group, or stands for $A-Si(Z^2)_{3-a}(OZ^1)_a$.

$Z^4$ stands for H or a monofunctional aromatic or cycloaliphatic or aliphatic group containing 1 to 8 C atoms.

$Z^5$ stands for a b-functional aromatic or aralphatic or cycloaliphatic or aliphatic group containing 1 to 40 C atoms, or for the group $A-Si(Z^2)_{3-a}(OZ^1)_a$.

In addition, X stands for O or S, a stands for 1 or 2 or 3, and b stands for 1 or 2 or 3 or 4.

Lastly, the condition applies that either $Z^3$ or $Z^4$ stands for H.

Thus, of the two groups $Z^3$ and $Z^4$ attached to the urea group (NCON) or thiourea group (NCSN), one, but not both, stands for H.

Namely, it is important for the invention that the urea group(s) or thiourea group(s) present in formula (I) is/are neither disubstituted nor tetrasubstituted, but, rather, is/are trisubstituted urea group(s) or thiourea group(s).

In the present document, use of the terms "independently" in conjunction with substituents, radicals, or groups is to be construed to mean that in the same molecule substituents, radicals, or groups which are denoted having the same meaning may at the same time be present with a different meaning.

In the entire present document, the prefixes "poly," for example in "polyisocyanate," "polythioisocyanate," "polyamine," "polyol," "polyphenol," and "polymercaptan," refer to molecules which formally contain two or more of the particular functional groups.

In the present document, an "impact modifier" is understood to mean an additive to an epoxy resin matrix which even at low addition quantities, in particular 0.1-50% by weight, preferably 0.5-40% by weight, results in a distinct increase in the toughness and which is therefore able to absorb fairly high impact or shock stress before the matrix ruptures or breaks.

The dashed lines in the formulas in the present document in each case represent the bond between the particular substituent and the associated molecular moiety.

In the present document, the term "polymer" includes on the one hand a collective of macromolecules produced by a polyreaction (polymerization, polyaddition, polycondensation) which are chemically uniform but different with regard to polymerization rate, molar mass, and chain length. On the other hand, the term also includes derivatives of such a collective of macromolecules from polyreactions, i.e., compounds obtained from reactions such as additions or substitutions, for example, of functional groups on specified macromolecules, and which may be chemically uniform or chemically nonuniform. The term further includes so-called "prepolymers," i.e., reactive oligomeric prepolymers, whose functional groups take part in the synthesis of macromolecules.

The term "polyurethane polymer" includes all polymers which are produced according to the so-called diisocyanate polyaddition process. This term also includes polymers which are practically or completely free of urethane groups. Examples of polyurethane polymers are polyether polyurethanes, polyester polyurethanes, polyether polyureas, polyureas, polyester polyureas, polyisocyanurates, and polycarbodiimides.

It is preferred that a stands for 2 or 3. Most preferably, a represents a value of 3.

The group A preferably represents an optionally branched alkylene group containing 1 to 4 C atoms. In particular, A stands for a methylene, propylene, n-butylene, or isobutylene group. A particularly preferably stands for a propylene group.

It is preferred that b stands for 1 or 2.

The methyl group is the preferred group for $Z^3$ or $Z^4$ or $Z^5$ as a monofunctional aliphatic group containing 1 to 8 C atoms.

It has been shown to be particularly advantageous when the silane of formula (I) contains no aromatic substituents.

If $Z^3$ stands for a monofunctional aromatic or cycloaliphatic or aliphatic group containing 1 to 8 C atoms, and which contains at least one carboxylate, nitrile, nitro, phosphonate, or sulfonic or sulfonate group, $Z^3$ in particular stands for the group of formula (III)

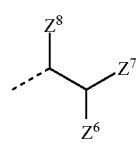
(III)

where
$Z^8$ and $Z^6$ independently stand for a hydrogen atom or for a radical selected from the group comprising —$Z^9$, —OOO$Z^9$, and —CN, and
$Z^7$ stands for a hydrogen atom or for a radical selected from the group comprising —$CH_2$—COO$Z^9$, —COO$Z^9$, —CONH$Z^9$, —CON($Z^9$)$_2$, —CN, —NO$_2$, —PO(O$Z^9$)$_2$, —SO$_2Z^9$, and —SO$_2$O$Z_9$,
where
$Z^9$ stands for a monofunctional hydrocarbon radical in particular containing 1 to 6 C atoms, and optionally containing at least one heteroatom.

The silanes of formula (I) may be easily synthesized in various ways.

In a first variant, an isocyanate or thioisocyanate of formula (II a) is reacted with a secondary aminosilane of formula (II b), i.e., in this case $Z^3$ being different from H, to produce the silane of formula (I).

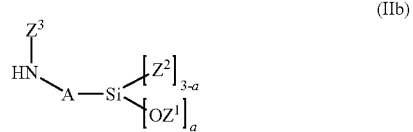

In a second variant, a secondary amine of formula (II c), i.e., in this case $Z^4$ being different from H, is reacted with an isocyanatosilane or thioisocyanatosilane of formula (II d) to produce the silane of formula (I).

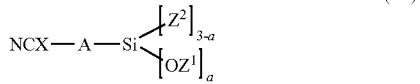

In a third variant, a compound of formula (II e) is reacted with an aminosilane of formula (II f) to produce the silane of formula (I).

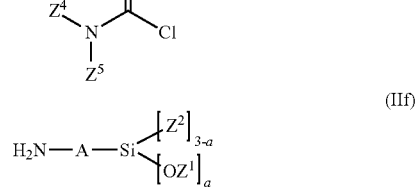

The first variant is suited in particular for producing silanes having multiple urea groups or thiourea groups, i.e., where b>1. The polyisocyanates necessary for this purpose are easily obtainable.

Mono- or polyisocyanates are suited as isocyanates of formula (II a). The mono- or polyisocyanates may be aromatic or aliphatic.

Examples of suitable aromatic polyisocyanates are monomeric di- or triisocyanates such as 2,4- and 2,6-toluoylene diisocyanate and any given mixtures of these isomers (TDI), 4,4'-, 2,4'-, and 2,2'-diphenylmethane diisocyanate and any given mixtures of these isomers (MDI), mixtures of MDI and MDI homologs (polymeric MDI or PMDI), 1,3- and 1,4-phenylene diisocyanate, 2,3,5,6-tetramethyl-1,4-diisocyanatobenzene, naphthalene-1,5-diisocyanate (NDI), 3,3'-dimethyl-4,4'-diisocyanatodiphenyl (TODI), dianisidine diisocyanate (DADI), 1,3,5-tris-(isocyanatomethyl)benzene, tris-(4-isocyanatophenyl)methane, tris-(4-isocyanatophenyl) thiophosphate, oligomers and polymers of the above-mentioned isocyanates, and any given mixtures of the above-mentioned isocyanates. MDI and TDI are preferred.

Examples of suitable aliphatic polyisocyanates are monomeric di- or triisocyanates such as 1,4-tetramethylene diisocyanate, 2-methylpentamethylene-1,5-diisocyanate, 1,6-hexamethylene diisocyanate (HDI), 2,2,4- and 2,4,4-trimethyl-1,6-hexamethylene diisocyanate (TMDI), 1,10-decamethylene diisocyanate, 1,12-dodecamethylene diisocyanate, lysine diisocyanate and lysine ester diisocyanate, cyclohexane-1,3- and -1,4-diisocyanate, 1-methyl-2,4- and -2,6-diisocyanatocyclohexane, and any given mixtures of these isomers (HTDI or $H_6$TDI), 1-isocyanato-3,3,5-trimethyl-5-isocyanatomethylcyclohexane (=isophorone diisocyanate or IPDI), perhydro-2,4'- and -4,4'-diphenylmethane diisocyanate (HMDI or $H_{12}$MDI), 1,4-diisocyanato-2,2,6-trimethylcyclohexane (TMCDI), 1,3- and 1,4-bis-(isocyanatomethyl)cyclohexane, m- and p-xylylene diisocyanate (m- and p-XDI), m- and p-tetramethyl-1,3- and -1,4-xylylene diisocyanate (m- and p-TMXDI), bis-(1-isocyanato-1-methylethyl)naphthalene, dimeric and trimeric fatty acid isocyanates such as 3,6-bis-(9-isocyanatononyl)-4,5-di-(1-heptenyl) cyclohexene (dimeryl diisocyanate), $\alpha,\alpha,\alpha',\alpha',\alpha'',\alpha''$-hexamethyl-1,3,5-mesitylene triisocyanate, oligomers and polymers of the above-mentioned isocyanates, and any given mixtures of the above-mentioned Isocyanates. HDI and IPDI are preferred.

In another embodiment, a polyisocyanate in the form of a monomeric di- or triisocyanate or an oligomer of a monomeric diisocyanate is suitable as polyisocyanate, the above-mentioned aromatic and aliphatic di- and triisocyanates, for example, being suitable as monomeric di- or triisocyanate. The oligomers of HDI, IPDI, and TDI are particularly suited as oligomers of a monomeric diisocyanate. In practice, such oligomers usually represent mixtures of substances having different oligomerization rates and/or chemical structures. The oligomers preferably have an average NCO functionality of 2.1 to 4.0, and contain in particular isocyanurate, iminooxadiazindione, uretdione, urethane, biuret, allophanate, carbodiimide, uretonimine, or oxadiazintrione groups. The oligomers preferably have a low content of monomeric diisocyanates. Commercially available types are in particular HDI biurets, for example DESMODUR N 100 and DESMODUR N 3200 (from Bayer), TOLONATE HDB and TOLONATE HDB-LV (from Rhodia), and DURANATE 24A-100 (from Asahi Kasei); HDI isocyanurates, for example DESMODUR N 3300, DESMODUR N 3600, and DESMODUR N 3790 BA (from Bayer), TOLONATE HDT, TOLONATE HDT-LV, and TOLONATE HDT-LV2 (from Rhodia), DURANATE TPA-100 and DURANATE THA-100 (from Asahi Kasei), and CORONATE HX (from Nippon Polyurethane); HDI uretdiones, for example DESMODUR N 3400 (from Bayer); HDI iminooxadiazindiones, for example DESMODUR XP 2410 (from Bayer); HDI allophanates, for example DESMODUR VP LS 2102 (from Bayer); IPDI isocyanurates, for example DESMODUR Z 4470 (from Bayer) and VESTANAT T1890/100 (from Evonik); TDI oligomers, for example DESMODUR IL (from Bayer); and mixed isocyanurates based on TDI/HDI, for example DESMODUR HL (from Bayer).

Particularly suited as monoisocyanates are butyl isocyanate, pentyl isocyanate, hexyl isocyanate, octyl isocyanate, decyl isocyanate, dodecyl isocyanate, octadecyl isocyanate, cyclohexyl isocyanate, methylcyclohexyl isocyanate, phenyl isocyanate, benzyl isocyanate, 2-methoxyphenyl isocyanate, or p-toluenesulfonyl isocyanate.

Mono- or polythioisocyanates are suitable as thioisocyanates of formula (II a). The mono- or polythioisocyanates may be aromatic or aliphatic.

Particularly suited as thioisocyanates are the compounds which are analogous to the above-mentioned mono- or polyisocyanates, and which contain thioisocyanate group(s) instead of isocyanate group(s).

The secondary aminosilanes of formula (II b) are sometimes commercially available, or may be prepared from an aminosilane of formula (II f), in particular by a Michael-type addition to a Michael acceptor of formula (III a) or (III b).

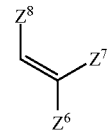

(IIIa)

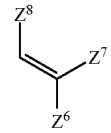

(IIIb)

In the present document, the term "Michael acceptor" refers to compounds which, due to their double bonds which are activated by electron acceptor radicals, are able to take part in a nucleophilic addition reaction with primary amino groups ($NH_2$ groups) in a manner analogous to the Michael addition (hetero-Michael addition).

Particularly preferred Michael acceptors of formula (III a) or (III b) are acrylonitrile, acrylates and methacrylates, acrylamides or methacrylamides, diesters of maleic acid and fumaric acid, citraconic acid diester, and itaconic acid diester.

Preferred secondary aminosilanes of formula (II b) which are thus obtained via a Michael-type addition are N-(3-trimethoxysilylpropyl)aminosuccinic acid dimethyl ester and diethyl ester, and the analogs thereof with ethoxy or isopropoxy groups instead of methoxy groups on the silicon atom, most preferably N-(3-trimethoxysilylpropyl)aminosuccinic acid diethyl ester.

Also particularly suited as secondary aminosilanes of formula (II b) are N-butyl-3-aminopropyltrimethoxysilane, N-phenyl-3-aminopropyltrimethoxysilane, N-butyl-3-aminopropyltriethoxysilane, and N-phenyl-3-aminopropyltriethoxysilane.

In one embodiment, a secondary aminosilane of formula (II b) in which $Z^3$ stands for A-Si($Z^2$)$_{3-a}$(OZ$^1$)$_a$ is used. Such secondary aminosilanes are preferably bis(3-trimethoxysilylpropyl)amine or bis(3-triethoxysilylpropyl)amine.

Particularly suited as secondary amine of formula (II c) are dimethylamine, diethylamine, di-n-propylamine, diisopropylamine, di-n-butylamine, diisobutylamine, di-sec-butylamine, dipentylamine, dihexylamine, di-2-ethylhexylamine, cyclohexylamine, cycloheptylamine, N-methylethylamine, N-methylbutylamine, N-ethylbutylamine, dicyclohexylamine, diphenylamine, and dibenzylamine.

Particularly suited as isocyanatosilane or thioisocyanatosilane of formula (II d) are those selected from the group comprising isocyanatomethyltrimethoxysilane, isocyanatomethyldimethoxymethylsilane, 3-isocyanatopropyltrimethoxysilane, 3-isocyanatopropyldimethoxymethylsilane, thioisocyanatomethyltrimethoxysilane, thioisocyanatomethyldimethoxymethylsilane, 3-thioisocyanatopropyltrimethoxysilane, 3-thioisocyanatopropyldimethoxymethylsilane, and the analogs thereof with ethoxy or isopropoxy groups instead of methoxy groups on the silicon atom. 3-Isocyanatopropyltrimethoxysilane and 3-thioisocyanatopropyltrimethoxysilane, in particular 3-isocyanatopropyltrimethoxysilane, are preferred as isocyanatosilane or thioisocyanatosilane of formula (II d).

The compounds of formula (II e) are easily obtainable or commercially available. N,N-Dimethylcarbamoyl chloride is particularly preferred as a compound of formula (II e).

Particularly suited as aminosilane of formula (II f) are aminosilanes selected from the group comprising 3-aminopropyltrimethoxysilane, 3-aminopropyldimethoxymethylsilane, 3-amino-2-methylpropyltrimethoxysilane, 4-aminobutyltrimethoxysilane, 4-aminobutyldimethoxymethylsilane, 4-amino-3-methylbutyltrimethoxysilane, 4-amino-3,3-dimethylbutyltrimethoxysilane, 4-amino-3,3-dimethylbutyldimethoxymethylsilane, 2-aminoethyltrimethoxysilane, 2-aminoethyldimethoxymethylsilane, aminomethyltrimethoxysilane, aminomethyldimethoxymethylsilane, aminomethylmethoxydimethylsilane, and the analogs thereof with ethoxy or isopropoxy groups instead of methoxy groups on the silicon atom. The aminosilane of formula (II f) is particularly preferably 3-aminopropyltrimethoxysilane, 3-aminopropyldimethoxymethylsilane, 3-aminopropyltriethoxysilane, or 3-aminopropyldiethoxymethylsilane.

Thus, for example, suitable silanes of formula (I) may be prepared as addition products of 3-aminopropyltrimethoxysilane with N,N-dimethylcarbamoyl chloride, of N-methyl-3-aminopropyltriethoxysilane with butyl isocyanate or HDI or IPDI, of N-cyclohexyl-3-aminopropyltrimethoxysilane with phenyl isocyanate or butyl isocyanate or HDI or MDI, of 3-isocyanatopropyltriethoxysilane with dimethylamine, of N-phenyl-3-aminopropyltriethoxysilane with butyl isocyanate or phenyl isocyanate, of N-phenyl-3-aminopropyltriethoxysilane with HDI or MDI, of bis(3-trimethoxysilylpropyl)amine with butyl isocyanate or phenyl isocyanate or HDI or MDI, of 3-aminopropylmethyldimethoxysilane with N,N-dimethylcarbamoyl chloride, or N-methyl-3-aminopropyldimethoxysilane with butyl isocyanate, phenyl isocyanate, HDI, or MDI.

On the one hand, particularly preferred are silanes of formula (I) in which b is different from 1 and $Z^4$ stands for H.

Specific silanes of formula (I), namely, silanes of formula (I a), are also the subject matter of the present invention.

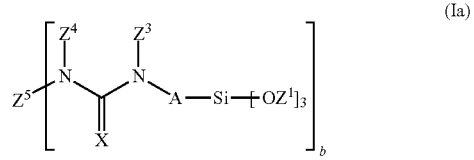

(Ia)

Silanes of formula (I a) may be divided into three classes:

The silanes are members of either a first class (class 1), a second class (class 2), or a third class (class 3).

In the class 1 silanes of formula (I a),
A is $CH_2$—$CH_2$—$CH_2$, $Z^1$ is $CH_3$, $Z^3$ is H, $Z^4$ is $CH_3$, $Z^5$ is $CH_3$, X is O, and b is 1.

In class 2 silanes of formula (I a),
A is $CH_2$—$CH_2$—$CH_2$, $Z^1$ is $CH_3$, $Z^3$ is $CH_3$, $Z^4$ is H, $Z^5$ is $CH_3$, X is O, and b is 1.

In class 3 silanes of formula (I a),
A is $CH_2$, $Z^1$ is $CH_3$ or $CH_2CH_3$, $Z^3$ is H, $Z^4$ is a monofunctional aliphatic group containing 1 to 12 C atoms, $Z^5$ is a monofunctional aliphatic group containing 1 to 12 C atoms, X is O, and b is 1.

For the sake of completeness, it is noted at this point that, due to the fact that these silanes of formula (I a) are selected silanes of formula (I), it is understood as a matter of course that statements made in the present document regarding silanes of formula (I) also apply for silanes of formula (I a), even if in the particular case direct reference is not made to formula (I a).

The silane of formula (I) may be used directly as a curing agent for epoxy resins which is activatable at elevated temperature, or the silane of formula (I) may be present on the surface of a substrate and used as a curing agent for epoxy resins which is activatable at elevated temperature. The surface of the substrate may be coated with the silane of formula (I), or may be derivatized, i.e., chemically bound, with same. The type of substrate primarily determines whether a coating or a derivatization of a surface of a substrate is possible using the silane of formula (I).

Thus, a substrate whose surface is coated or derivatized with silane of formula (I) is also the subject matter of the present invention.

Silane groups, such as those present in the silane of formula (I), have at least one Si—O—$Z^1$ functionality, and under the influence of water hydrolyze to form silanol groups (—Si—OH). Such silanol groups are then able to condense with surface groups, in particular surface OH groups, resulting in chemical binding of the silane of formula (I) to the surface of the substrate (=derivatization of the surface of the substrate with the silane of formula (I)). It is of course clear to one skilled in the art that silanol groups may also condense with one another, possibly forming siloxanes. Depending on the substrate, however, the silane may also be present unchanged at the surface of the substrate.

By using a silane of formula (I) which is bound to or present on a surface, this silane is continuously, or at least temporarily, immobilized on the substrate surface. Such immobilization has the advantage that the curing agent may be used selectively at certain locations.

Fillers on the one hand and flat substrates on the other hand are primarily used as such a substrate.

In one preferred embodiment the substrate is a flat substrate. Such flat substrates are in particular those which are to be adhesively bonded. For example, such flat substrates are planar substrates such as sheets, disks, or flanges; or arched substrates such as fenders, headlight housings, pipes, or cavities.

One particularly suitable application of such coated or derivatized flat substrates is the following method for adhesive bonding, comprising the following steps:

α) Applying a silane of formula (I) to the surface of a flat substrate to be adhesively bonded;

β) Applying an epoxy resin composition containing at least one epoxy resin EH, having on average more than one epoxide group per molecule, to the surface which is coated or derivatized with silane of formula (I);

γ) Contacting the epoxy resin composition with another surface of a substrate to be adhesively bonded;

δ) Heating the flat substrate and/or the epoxy resin composition to a temperature of 100-220° C., in particular 120-200° C., preferably 160-190° C.

As the result of heating the flat substrate and/or the epoxy resin composition in step δ), the heat-activatable curing agent, i.e., the silane or derivative thereof present on the surface of the flat substrate, is activated and brings about curing of the epoxy resin which is thus in contact. This further heating of the epoxy resin composition as the result of this curing reaction then brings about curing of the epoxy resin composition at a farther distance from the substrate surface, and so forth. Selective curing of the epoxy resin adhesive composition, starting from the substrate, may thus be carried out, which sometimes results in an intentional and selectively producible gradient in the mechanical properties of the epoxy adhesive. If the surface of the substrate from step γ) is likewise coated or derivatized with silane of formula (I), bonding composites may be obtained whose adhesive has different mechanical properties in the core than at the border for the particular substrate.

The application of the silane of formula (I) to the surface of the flat substrate to be adhesively bonded in step α) may be carried out using a solvent, for example, and optionally in the presence of catalysts for hydrolysis of the Si—O—$Z^1$ groups of the silane of formula (I) and/or condensation of silanol groups hydrolysis. Such catalysts are well known to persons skilled in the art in the field of silanes. A mixture of a silane with a volatile solvent and optionally a catalyst, in particular an organic acid, is typically used. Water, alcohols, ketones, aldehydes, carboxylic acid esters, and hydrocarbons in particular are used as solvent. The boiling point at standard pressure is in particular 100° C. or less. Particularly preferred solvents for this purpose are methanol, ethanol, isopropanol, hexane, heptane, and methyl ethyl ketone. The application may be carried out in particular by spraying, sprinkling, wiping, brushing, rolling, or dipping. The application is preferably made with a small layer thickness, typically less than 100 microns.

It is advantageous for a time period of at least 1 minute, typically between 5 minutes and 30 minutes, to elapse between step α) and step β). This is particularly advantageous when the silane in step α) is applied in a solvent. The solvent is able to completely or at least substantially evaporate during this time period. The layer thickness of the silane present on the surface is preferably less than 100 microns before the start of step β).

In an even more preferred embodiment, the substrate which is coated or derivatized with silane of formula (I) is a filler, preferably an inorganic filler, in particular an inorganic filler containing Ca and/or Si and/or Al atoms, preferably Si and/or Al atoms.

Particularly suited fillers of this type are calcium carbonate, silica, in particular pyrogenic silicic acid, kaolin, aluminum hydroxide, aluminum oxide, and alumoxane. Pyrogenic silicic acid and alumoxane are most preferred. The filler is preferably dry, or at least moist only at the surface. To obtain a homogeneous surface coating or derivatization, it is particularly advantageous when the filler is free-flowing.

The filler is coated or derivatized in the same manner as described above for the coating or derivatization of flat substrates in step α). However, the filler may also be stirred into the silane of formula (I), preferably into a mixture including silane (I), at least one of the above-mentioned solvents, and optionally an above-mentioned catalyst, and then filtered off after the coating or derivatization. It is also preferable for a given time period of at least 1 minute, typically between 5 minutes and 30 minutes, to elapse between application of the silane of formula (I) and use of the filler in or for epoxy resin compositions.

It is important that for the substrate which is coated or derivatized with silane of formula (I), only the surface is coated or derivatized; i.e., any processes in which the silane of formula (I) is used directly for production of the filler, for example for the production of sol gels or xerogels, are not the subject matter of the invention. Namely, it is important for the essence of the invention that only the surface is coated or derivatized. On the one hand, existing fillers may be used which are easily commercially obtainable and above all inexpensive. On the other hand, the coating or derivatization of the substrates is a very easily managed process, while the processes of in situ filler production, for example for sol gels or xerogels, are very complicated, expensive, and susceptible to error.

These fillers are particularly preferably fine fillers; i.e., the average particle size of the filler is preferably less than 50 microns, in particular less than 1 micron. So-called nanofillers having an average particle size of 1 nanometer to 1 micron are most preferred.

The above-described silanes of formula (I) or fillers coated or derivatized with silane of formula (I) are in particular part of a thermosetting epoxy resin composition.

Therefore, in a further aspect the present invention relates to a thermosetting epoxy resin composition containing
  at least one epoxy resin EH having an average of more than one epoxide group per molecule;
  at least one silane of formula (I) or a filler whose surface is coated or derivatized with silane of formula (I), as described in detail above.

The epoxy resin EH having an average of more than one epoxide group per molecule is preferably a liquid epoxy resin or a solid epoxy resin. The term "solid epoxy resin" is well known to a person skilled in the art in the field of epoxides, and is used in contrast to "liquid epoxy resins." The glass [transition] temperature of solid resins is above room temperature; i.e., the solid resins may be comminuted at room temperature to form free-flowing powders.

Preferred solid epoxy resins have formula (V):

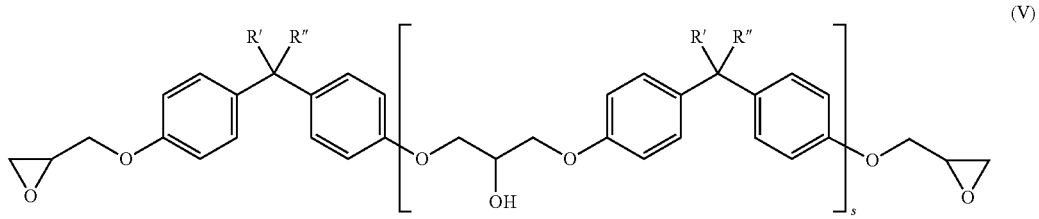

In this regard, substituents R' and R" independently stand for either H or CH$_3$. In addition, subscript s stands for a value of >1.5, in particular 2 to 12.

Such solid epoxy resins are commercially available, for example from Dow, Huntsman, or Hexion.

Compounds of formula (V) having a subscript s between 1 and 1.5 are referred to by those skilled in the art as "semisolid epoxy resins." For the present invention they are also regarded as solid resins. However, solid epoxy resins in the narrower sense, i.e., for which subscript s has a value of >1.5, are preferred.

Preferred liquid epoxy resins have formula (VI):

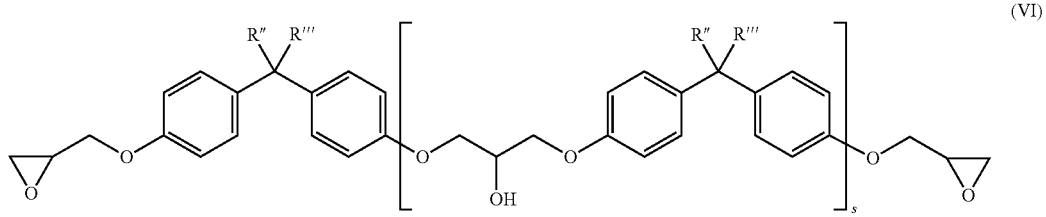

(VI)

In this regard, substituents R' and R" independently stand for either H or CH$_3$. In addition, subscript r stands for a value of 0 to 1. It is preferred that r stands for a value less than 0.2.

These are preferably diglycidyl ethers of bisphenol-A (DGEBA), of bisphenol-F, and of bisphenol-A/F. Such liquid resins are available, for example, as ARALDITE GY 250, ARALDITE PY 304, ARALDITE GY 282 (Huntsman), D.E.R. 331 or D.E.R. 330 (Dow), or Epikote 828 (Hexion).

Also suited as epoxy resin EH are so-called novolacs, which in particular have the following formula:

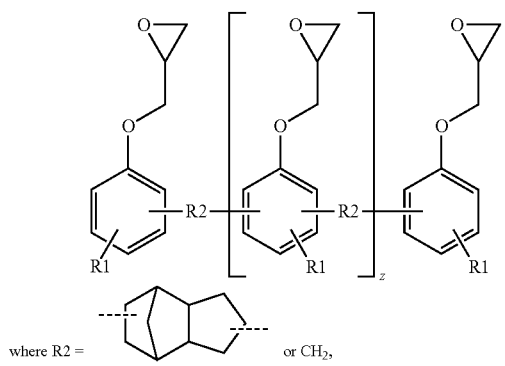

R1=H or methyl, and z=0 to 7.

These are in particular phenol or cresol novolacs (R2=CH$_2$).

Such epoxy resins are commercially available under the trade names EPN or ECN as well as TACTIX 556 from Huntsman, or under the D.E.N. product series from Dow Chemical.

The epoxy resin EH preferably represents a liquid epoxy resin of formula (VI). In an even more preferred embodiment, the thermosetting epoxy resin composition contains at least one liquid epoxy resin of formula (VI) and at least one solid epoxy resin of formula (V).

The fraction of epoxy resin EH is preferably 10-85% by weight, in particular 15-70% by weight, preferably 15-60% by weight, relative to the weight of the thermosetting epoxy resin composition.

The fraction of the silane of formula (I) or of the filler whose surface is coated or derivatized with silane of formula (I) in the composition is advantageously selected in such a way that the silane of formula (I) or the silane fraction of the filler is 0.001-20% by weight, in particular 0.1-15% by weight, preferably 0.5-10% by weight, relative to the weight of the thermosetting epoxy resin composition. For the sake of clarity, it is noted at this point that in addition to the silane which is present on the filler as silane of formula (I), the silane of formula (I) which is chemically bound to the filler is considered as "silane" for the term "silane fraction of the filler." Thus, for determining the silane fraction of the filler it is immaterial whether the silane at the surface of the filler is free or chemically bound, i.e., whether the filler is coated or derivatized with silane of formula (I).

The composition according to the invention also preferably contains at least one heat-activatable curing agent B which in particular is selected from the group comprising dicyandiamide, guanamine, guanidine, aminoguanidine, and derivatives thereof; substituted ureas, in particular 3-(3-chloro-4-methylphenyl)-1,1-dimethylurea (chlortoluron), or phenyldimethyl ureas, in particular p-chlorophenyl-N,N-dimethylurea (monuron), 3-phenyl-1,1-dimethylurea (fenuron), 3,4-dichlorphenyl-N,N-dimethylurea (diuron), N,N-dimethylurea, N-isobutyl-N',N'-dimethylurea, 1,1'-(hexane-1,6-diyl)bis(3,3'-dimethylurea), and imidazoles, imidazole salts, imidazolines, and amine complexes.

This heat-activatable curing agent B may be activated at the same or a different temperature as the silane of formula (I).

Dicyandiamide is particularly preferred as curing agent B.

The total fraction of curing agent B is advantageously 1-10% by weight, preferably 2-8% by weight, relative to the weight of the overall composition.

The thermosetting epoxy resin composition may also contain a thixotropic agent C based on a urea derivative. The urea derivative in particular is a reaction product of an aromatic monomeric diisocyanate with an aliphatic amine compound. It is also possible to react multiple different monomeric diisocyanates with one or more aliphatic amine compounds, or to react a monomeric diisocyanate with multiple aliphatic amine compounds. The reaction product of 4,4'-diphenylmethylene diisocyanate (MDI) with butylamine has proven to be particularly advantageous.

The urea derivative is preferably present in a carrier material. The carrier material may be a softener, in particular a phthalate or an adipate, preferably a diisodecyl phthalate (DIDP) or dioctyl adipate (DOA). The carrier agent may also be a nondiffusing carrier agent. This is preferred in order to ensure minimum migration of unreacted constituents after curing. Blocked polyurethane prepolymers are preferred as nondiffusing carrier agents.

The preparation of such preferred urea derivatives and carrier materials is described in detail in patent application US 2002/0007003 A1, the content of which is hereby incorporated by reference. The carrier material is advantageously a blocked polyurethane prepolymer, in particular obtained by reacting a trifunctional polyether polyol with IPDI, followed by blocking of the end-position isocyanate groups with ε-caprolactam.

The total proportion of thixotropic agent C is advantageously 0-40% by weight, preferably 5-25% by weight, relative to the weight of the overall composition. The ratio of the weight of the urea derivative to the weight of the optionally present carrier agent is preferably 2/98 to 50/50, in particular 5/95 to 25/75.

It has also been shown to be particularly advantageous when the thermosetting single-component epoxy resin composition also contains at least one impact modifier D.

The impact modifiers D may be solid or liquid.

It has been shown that the impact modifier D is advantageously selected from the group comprising blocked polyurethane polymers, liquid rubbers, epoxy resin-modified liquid rubbers, block copolymers, and core-shell polymers, in particular in a quantity of 0.1-50% by weight, in particular 0.5-35% by weight, preferably 1-20% by weight, relative to the weight of the thermosetting epoxy resin composition.

In one embodiment, this impact modifier D is a liquid rubber D1 which is a carboxyl- or epoxide-terminated acrylonitrile/butadiene copolymer or a derivative thereof. Such liquid rubbers are commercially available, for example under the names HYPRO (formerly HYCAR) CTBN, CTBNX, and ETBN from Nanoresins AG, Germany, or from Emerald Performance Materials LLC. Elastomer-modified prepolymers containing in particular epoxy groups, as marketed under the product line POLYDIS, preferably the product line POLYDIS 36. from Struktol (Schill+Seilacher Groups, Germany), or under the product line Albipox (Nanoresins, Germany), are suitable as derivatives.

In another embodiment, the impact modifier D is a polyacrylate liquid rubber D2 which is fully miscible with liquid epoxy resins and which does not demix to form microdroplets until the epoxy resin matrix has cured. Such polyacrylate liquid rubbers are available, for example, under the trade name 20208-XPA from Rohm and Haas.

It is clear to one skilled in the art that mixtures of liquid rubbers may of course also be used, in particular mixtures of carboxyl- or epoxide-terminated acrylonitrile/butadiene copolymers or derivatives thereof with epoxide-terminated polyurethane prepolymers.

In another embodiment, the impact modifier D is a solid impact modifier which is an organic ion-exchanged layered mineral DE1.

The ion-exchanged layered mineral DE1 may be either a cation-exchanged layered mineral DE1c or an anion-exchanged layered mineral DE1a.

The cation-exchanged layered mineral DE1c is obtained from a layered mineral DE1' in which at least a portion of the cations have been exchanged with organic cations. Examples of such cation-exchanged layered minerals DE1c are in particular those mentioned in U.S. Pat. No. 5,707,439 or U.S. Pat. No. 6,197,849. The cited documents also describe the method for producing these cation-exchanged layered minerals DE1c. A layered silicate is preferred as layered mineral DE1'. The layered mineral DE1' is particularly preferably a phyllosilicate, in particular a bentonite, as described in U.S. Pat. No. 6,197,849, column 2, line 38 to column 3, line 5. A layered mineral DE1' such as kaolinite, a montmorillionite, a hectorite, or an illite has been shown to be particularly suitable.

At least a portion of the cations in the layered mineral DE1' are replaced by organic cations. Examples of such cations include n-octylammonium, trimethyldodecylammonium, dimethyldodecylammonium, or bis(hydroxyethyl)octadecylammonium, or similar derivatives of amines which may be obtained from natural fats and oils; or guanidinium cations or amidinium cations; or cations of the N-substituted derivatives of pyrrolidine, piperidine, piperazine, morpholine, or thiomorpholine; or cations of 1,4-diazobicyclo[2.2.2]octane (DABCO) and 1-azobicyclo[2.2.2]octane; or cations of N-substituted derivatives of pyridine, pyrrole, imidazole, oxazole, pyrimidine, quinoline, isoquinoiline, pyrazine, indole, benzimidazole, benzoxaziole, thiazole, phenazine, and 2,2'-bipyridine. Also suitable are cyclic amidinium cations, in particular those disclosed in U.S. Pat. No. 6,197,849 in column 3, line 6 to column 4, line 67. Compared to linear ammonium compounds, cyclic ammonium compounds are characterized by increased thermal stability since they are not able to undergo the thermal Hoffmann degradation reaction.

Preferred cation-exchanged layered minerals DE1c are known to one skilled in the art under the term "organoclay" or "nanoclay," and are commercially available, for example, under the group names TIXOGEL or NANOFIL (Sudchemie), CLOISITE (Southern Clay Products), NANOMER (Nanocor Inc.), or GARMITE (Rockwood).

The anion-exchanged layered mineral DE1a is obtained from a layered mineral DE1'' in which at least a portion of the anions have been exchanged with organic anions. One example of such an anion-exchanged layered mineral DE1a is a hydrotalcite DE1'', in which at least a portion of the carbonate anions of the intermediate layers have been exchanged with organic anions.

It is also possible for the composition to contain both a cation-exchanged layered mineral DE1c and an anion-exchanged layered mineral DE1a.

In another embodiment, the impact modifier D is a solid impact modifier which is a block copolymer DE2. The block copolymer DE2 is obtained from an anionic polymerization or controlled radical polymerization of methacrylate with at least one further monomer containing an olefinic double bond. Particularly preferred as monomers containing an olefinic double bond are monomers in which the double bond is directly conjugated with a heteroatom or with at least one further double bond. Particularly suited are monomers selected from the group comprising styrene, butadiene, acrylonitrile, and vinyl acetate. Acrylate/styrene/acrylic acid copolymers (ASA), obtainable under the name GELOY 1020 from GE Plastics, for example, are preferred.

Particularly preferred block copolymers DE2 are block copolymers of methyl methacrylate, styrene, and butadiene. Such block copolymers are available, for example, as triblock copolymers under the group name SBM from Arkema.

In another embodiment, impact modifier D is a core-shell polymer DE3. Core-shell polymers are composed of an elastic core polymer and a rigid shell polymer. Particularly suited core-shell polymers are composed of a core of elastic acrylate polymer or butadiene polymer which encloses a rigid shell of an inflexible thermoplastic polymer. This core-shell structure is formed either spontaneously as the result of demixing of a block copolymer, or is specified by the polymerization control as latex or suspension polymerization with subsequent grafting. Preferred core-shell polymers are so-called MBS polymers, which are commercially available under the trade names CLEARSTRENGTH from Atofina, PARALOID from Rohm and Haas, or F-351 from Zeon.

Core-shell polymer particles which are already present as dried polymer latex are particularly preferred. Examples of such include GENIOPERL M23A from Wacker, having a polysiloxane core and an acrylate shell, radiation-crosslinked rubber particles of the NEP series manufactured by Eliokem, Nanoprene from Lanxess, or Paraloid EXL from Rohm and Haas.

Further comparable examples of core-shell polymers are marketed under the name ALBIDUR from Nanoresins AG, Germany.

Also suitable are nanoscale silicates in an epoxy matrix, marketed under the trade name NONOPDX from Nanoresins AG, Germany.

In another embodiment, the impact modifier D is a product DE4 of the reaction of a carboxylated solid nitrile rubber with excess epoxy resin.

In another embodiment, the impact modifier D is a blocked polyurethane polymer of formula (IV).

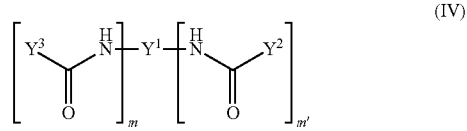

(IV)

In this regard, m and m' each stand for values between 0 and 8, with the condition that m+m' stands for a value from 1 to 8.

m is preferably different from 0.

In addition, $Y^1$ stands for a linear or branched polyurethane polymer PU1, terminated by m+m' isocyanate groups, after removal of all end-position isocyanate groups.

$Y^2$ independently stands for a blocking group which cleaves at a temperature above 100° C.

$Y^3$ independently stands for a group of formula (IV').

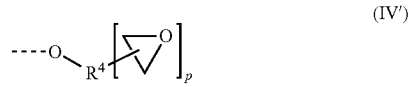

(IV')

In this regard, $R^4$ stands for a radical of an aliphatic, cycloaliphatic, aromatic, or araliphatic epoxy, containing a primary or secondary hydroxyl group, after removal of the hydroxide and epoxy groups, and p stands for the values 1, 2, or 3.

In the present document, "araliphatic radical" refers to an aralkyl group, i.e., an alkyl group substituted with aryl groups (see "Aralkyl," Römpp, CD Römpp's Chemical Lexicon, Version 1, Stuttgart/New York, Georg Thieme Verlag 1995).

In particular, $Y^2$ independently stands for a substituent selected from the group comprising

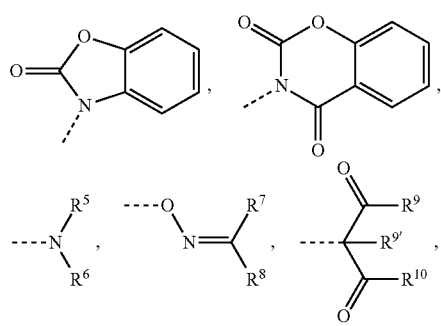

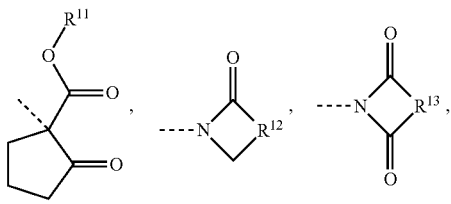

-continued

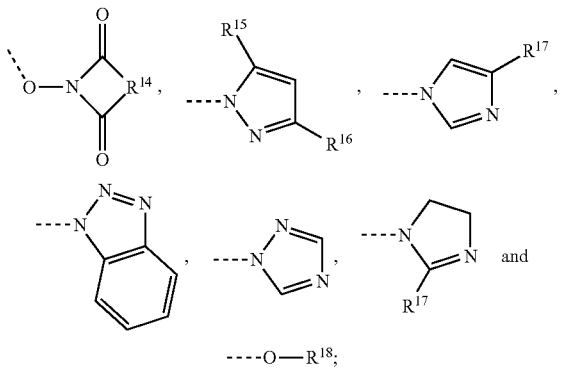

In this regard $R^5$, $R^6$, $R^7$, and $R^8$ each independently stand for an alkyl, cycloalkyl, aralkyl, or arylalkyl group, or $R^5$ together with $R^6$, or $R^7$ together with $R^8$, forms a part of a 4- to 7-membered ring which is optionally substituted.

In addition, $R^9$, $R^{9'}$, and $R^{10}$ each independently stand for an alkyl, aralkyl, or arylalkyl group or for an alkyloxy, aryloxy, or aralkyloxy group, and $R^{11}$ stands for an alkyl group.

$R^{12}$, $R^{13}$, and $R^{14}$ each independently stand for an alkylene group containing 2 to 5 C atoms, and optionally having double bonds or being substituted, or stand for a phenylene group or a hydrogenated phenylene group, and $R^{15}$, $R^{16}$, and $R^{17}$ each independently stand for H or for an alkyl, aryl, or aralkyl group.

Lastly, $R^{18}$ stands for an aralkyl group or for a mononuclear substituted or unsubstituted aromatic group which optionally contains aromatic hydroxyl groups. On the one hand, $R^{18}$ in particular represents phenols or bisphenols after removal of a hydroxyl group. Preferred examples of such phenols and bisphenol are in particular phenol, cresol, resorcinol, pyrocatechol, cardanol (3-pentadecenylphenol (from cashew shell oil)), nonylphenol, phenols reacted with styrene or dicyclopentadiene, bis-phenol-A, bis-phenol-F, and 2,2'-diallyl bisphenol-A.

On the other hand, $R^{18}$ in particular represents hydroxybenzyl alcohol and benzyl alcohol after removal of a hydroxyl group.

If $R^5$, $R^6$, $R^7$, $R^8$, $R^9$, $R^{9'}$, $R^{10}$, $R^{11}$, $R^{15}$, $R^{16}$, or $R^{17}$ stands for an alkyl group, this group in particular is a linear or branched $C_1$-$C_{20}$-alkyl group.

If $R^5$, $R^6$, $R^7$, $R^8$, $R^9$, $R^{9'}$, $R^{10}$, $R^{15}$, $R^{16}$, $R^{17}$, or $R^{18}$ stands for an aralkyl group, this group in particular is an aromatic group, in particular a benzyl group, bonded via methylene.

If $R^5$, $R^6$, $R^7$, $R^8$, $R^9$, $R^{9'}$, or $R^{10}$ stands for an alkylaryl group, this group in particular is a $C_1$-$C_{20}$-alkyl group, for example tolyl or xylyl, bonded via phenylene.

Particularly preferred $Y^2$ radicals are radicals selected from the group comprising

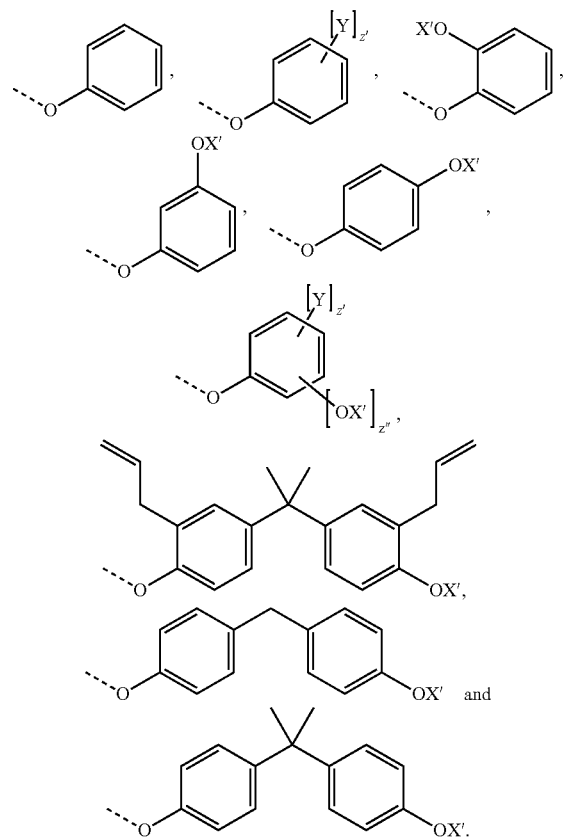

In this regard, the radical Y stands for a saturated or olefinically unsaturated hydrocarbon radical containing 1 to 20 C atoms, in particular 1 to 15 C atoms. Allyl, methyl, nonyl, dodecyl, or an unsaturated $C_{15}$-alkyl radical containing 1 to 3 double bonds is particularly preferred as Y.

The radical X' stands for H or for an alkyl, aryl, or aralkyl group, in particular for H or methyl.

The subscripts z' and z" stand for the values 0, 1, 2, 3, 4, or 5, with the condition that the sum z'+z" is a value between 1 and 5.

The blocked polyurethane polymer of formula (IV) is prepared by [reacting] linear or branched polyurethane polymers PU1, terminated by the isocyanate groups, with one or more isocyanate-reactive compounds $Y^2H$ and/or $Y^3H$. If more than one such isocyanate-reactive compound is used, the reaction may be carried out sequentially or using a mixture of these compounds.

The reaction is carried out in such a way that the one or more isocyanate-reactive compounds $Y^2H$ and/or $Y^3H$ are used stoichiometrically or in stoichiometric excess to ensure that all NCO groups are reacted.

The isocyanate-reactive compound $Y^3H$ is a monohydroxyl epoxy compound of formula (IVa).

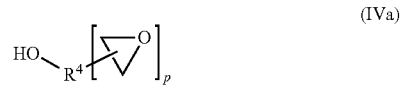

(IVa)

If more than one such monohydroxyl epoxy compound is used, the reaction may be carried out sequentially or using a mixture of these compounds.

The monohydroxyl epoxy compound of formula (IVa) contains 1, 2, or 3 epoxy groups. The hydroxyl group of this monohydroxyl epoxy compound (IVa) may represent a primary or a secondary hydroxyl group.

Such monohydroxyl epoxy compounds may be prepared, for example, by reacting polyols with epichlorohydrin. Depending on the reaction control, the corresponding monohydroxyl epoxy compounds are also formed in various concentrations as by-products in the reaction of polyfunctional alcohols with epichlorohydrin. These by-products may be isolated using customary separating operations. However, it is generally sufficient to use the product mixture, composed of polyol, which is completely and partially reacted to form the glycidyl ether, obtained in the glycidylization reaction of polyols. Examples of such hydroxyl-containing epoxides are butanediol monoglycidyl ether (present in butanediol diglycidyl ether), hexanediol monoglycidyl ether (present in hexanediol diglycidyl ether), cyclohexanedimethanol glycidyl ether, trimethylolpropane diglycidyl ether (present as a mixture in trimethylolpropane triglycidyl ether), glycerin diglycidyl ether (present as a mixture in glycerin triglycidyl ether), and pentaerythrite triglycidyl ether (present as a mixture in pentaerythrite tetraglycidyl ether). Preferably used is trimethylolpropane triglycidyl ether, which is present in a relatively high proportion in commonly prepared trimethylolpropane triglycidyl ethers.

However, other similar hydroxyl-containing epoxides, in particular glycidol, 3-glycidyloxybenzyl alcohol, or hydroxymethylcyclohexene oxide, may also be used. Also preferred is the β-hydroxy ether of formula (IVb), which is contained in proportions up to approximately 15% in commercially available liquid epoxy resins produced from bisphenol-A (R=$CH_3$) and epichlorohydrin, as well as the corresponding β-hydroxy ethers of formula (IVb), which are formed when bisphenol-F (R=H) or the mixture of bisphenol-A and bisphenol-F is reacted with epichlorohydrin.

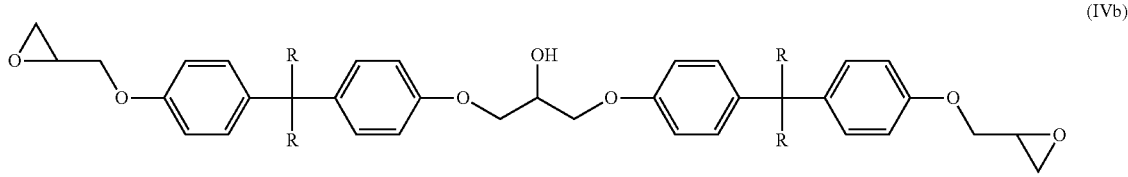

(IVb)

Also preferred are distillation residues which are produced in the preparation of high-purity distilled liquid epoxy resins. Such distillation residues have a concentration of hydroxyl-containing epoxides that is one to three times higher than in commercially available undistilled liquid epoxy resins. In addition, various epoxides may be used which contain a β-hydroxy ether group, prepared by the reaction of (poly-)epoxides with a deficit of monofunctional nucleophiles such as carboxylic acids, phenols, thiols, or secondary amines.

The R⁴ radical particularly preferably is a trifunctional radical of formula

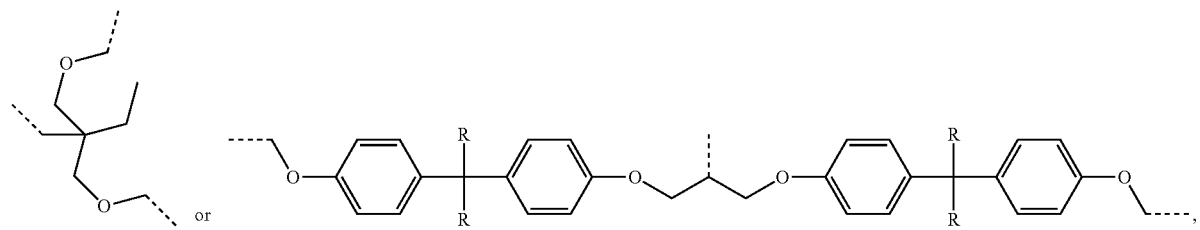

where R stands for methyl or H.

The free primary or secondary OH functionality of the monohydroxyl epoxide compound of formula (IVa) allows an efficient reaction with terminal isocyanate groups of polymers without having to use disproportionate excesses of the epoxide component.

The polyurethane polymer PU1, based on $Y^1$, may be prepared from at least one diisocyanate or triisocyanate and at least one polymer $Q_{PM}$ containing end-position amino, thiol, or hydroxyl groups, and/or from an optionally substituted polyphenol $Q_{PP}$.

Examples of suitable diisocyanates include aliphatic, cycloaliphatic, aromatic, or araliphatic diisocyanates, in particular those previously mentioned as diisocyanate of formula (II a). HDI, IPDI, MDI, or TDI are preferred.

Examples of suitable triisocyanates are trimers or biurets of aliphatic, cycloaliphatic, aromatic, or araliphatic diisocyanates, in particular the isocyanates and biurets previously mentioned as polyisocyanates of formula (II a).

Of course, suitable mixtures of di- or triisocyanates may also be used.

Polymers $Q_{PM}$ containing two or three end-position amino, thiol, or hydroxyl groups are particularly suited as polymers $Q_{PM}$ containing end-position amino, thiol, or hydroxyl groups.

Particularly suited as polymers $Q_{PM}$ are those disclosed, for example, in WO 2008/049857 A1, in particular as $Q_{PM}$ on page 7, line 25 to page 11, line 20, the content of which is in particular incorporated by reference.

The polymers $Q_{PM}$ advantageously have an equivalent weight of 300-6000, in particular 600-4000, preferably 700-2200, g/equivalent NCO-reactive groups.

Particularly suited as polymers $Q_{PM}$ are polyoxyalkylene polyols, also referred to as polyether polyols, hydroxy-terminated polybutadiene polyols, styrene-acrylonitrile grafted polyether polyols, polyhydroxy-terminated acrylonitrile/butadiene copolymers, polyester polyols, and polycarbonate polyols.

Amphiphilic block copolymers containing at least one hydroxyl group, in particular those marketed under the trade name FORTEGRA, in particular FORTEGRA 100, from Dow Chemical, have proven to be particularly suitable as polymers $Q_{PM}$.

Particularly suited as polyphenol $Q_{PP}$ are bis-, tris-, and tetraphenols. These are understood to mean not only pure phenols but also optionally substituted phenols. Various types of substitution may be used. This is understood in particular to mean a substitution directly at the aromatic nucleus to which the phenolic OH group is bound. In addition, the term "phenols" refers not only to mononuclear aromatics, but also to polynuclear or condensed aromatics or heteroaromatics which contain the phenolic OH group directly on the aromatic or heteroaromatic.

The bis- and trisphenols are particularly suited. Examples of suitable bisphenols or trisphenols include 1,4-dihydroxybenzene, 1,3-dihydroxybenzene, 1,2-dihydroxybenzene, 1,3-dihydroxytoluene, 3,5-dihydroxybenzoate, 2,2-bis(4-hydroxyphenyl)propane (=bisphenol-A), bis(4-hydroxyphenyl)methane (=bisphenol-F), bis(4-hydroxyphenyl)sulfone (=bisphenol-S), naphthoresorcinol, dihydroxynaphthalene, dihydroxyanthraquinone, dihydroxybiphenyl, 3,3-bis(p-hydroxyphenyl)phthalide, 5,5-bis(4-hydroxyphenyl)hexahydro-4,7-methanoindan, phenolpthalein, fluorescein, 4,4'-[bis-(hydroxyphenyl)-1,3-phenylene-bis-(1-methylethylidene)] (=bisphenol-M), 4,4'-[bis-(hydroxyphenyl)-1,4-phenylene-bis-(1-methylethylidene)] (=bisphenol-P), 2,2'-diallyl bisphenol-A, diphenols and dicresols prepared by reacting phenols or cresols with di-isopropylidenebenzene, phloroglucin, gallic acid esters, phenol or cresol novolacs having an OH functionality of 2.0 to 3.5, and all isomers of the above-mentioned compounds.

Particularly suited as impact modifier D which is optionally present in the composition are those disclosed in the following articles or patent documents, whose content is hereby incorporated by reference: EP 0 308 664 A1, in particular formula (I), especially page 5, line 14 to page 13, line 24; EP 0 338 985 A1, EP 0 353 190 A1, WO 00/20483 A1, in particular formula (I), especially page 8, line 18 to page 12, line 2; WO 01/94492 A1, in particular the reaction products referred to as D) and E), especially page 10, line 15 to page 14, line 22; WO 03/078163 A1, in particular the acrylate-terminated polyurethane resin referred to as B), especially page 14, line 6 to page 14, line 35; WO 2005/007766 A1, in particular formula (I) or (II), especially page 4, line 5 to page 11, line 20; EP 1 728 825 A1, in particular formula (I), especially page 3, line 21 to page 4, line 47; WO 2006/052726 A1, in particular the amphiphilic block copolymer referred to as b), especially page 6, line 17 to page 9, line 10; WO 2006/052729 A1, in particular the amphiphilic block copolymer referred to as b), especially page 6, line 25 to page 10, line 2; T. J. Hermel-Davidock et al., J. Polym. Sci. Part B: Polym. Phys. 2007, 45, 3338-3348, in particular the amphiphilic block copolymers, especially page 3339, column 2 to page 3341, column 2; WO 2004/055092 A1, in particular formula (I), especially page 7, line 28 to page 13, line 15; WO 2005/007720 A1, in particular formula (I), especially page 8, line 1 to page 17, line 10; WO 2007/020266 A1, in particular formula (I), especially page 3, line 1 to page 11, line 6; WO 2008/049857 A1, in particular formula (I), especially page 3, line 5 to page 6, line 20; WO 2008/049858 A1, in particular formulas (I) and (II), especially page 6, line 1 to page 12, line 15; WO 2008/049859 A1, in particular formula (I), especially page 6, line 1 to page 11, line 10; WO 2008/049860 A1, in particular formula (I), especially page 3, line 1 to page 9, line 6; and DE-A-2 123 033, US 2008/0076886 A1, WO 2008/016889, and WO 2007/025007.

It has been shown that multiple impact modifiers are advantageously present in the composition.

The fraction of impact modifiers D is advantageously used in a quantity of 1-45% by weight, in particular 1-35% by weight, relative to the weight of the composition.

In another preferred embodiment, the composition also contains at least one filler F. Preferred as such are mica, talc, kaolin, wollastonite, feldspar, syenite, chlorite, bentonite, montmorillonite, calcium carbonate (precipitated or pulverized), dolomite, quartz, silicic acids (pyrogenic or precipitated), cristobalite, calcium oxide, aluminum hydroxide, magnesium oxide, hollow ceramic beads, hollow glass beads, organic hollow beads, glass beads, and colored pigments. The organically coated as well as uncoated forms, which are commercially available and known to one skilled in the art, are also intended as filler F.

Functionalized alumoxanes as described in U.S. Pat. No. 6,322,890, for example, represent another example.

The overall fraction of the total filler F is advantageously 3-50% by weight, preferably 5-35% by weight, in particular 5-25% by weight, relative to the weight of the overall composition.

In another preferred embodiment the composition contains a physical or chemical blowing agent, such as those available, for example, under the trade names EXPANCEL from Akzo Nobel or CELOGEN from Chemtura. The proportion of blowing agent is advantageously 0.1-3% by weight, relative to the weight of the composition.

In another preferred embodiment, the composition also contains a reactive diluent G containing at least one epoxide group. These reactive diluents G are in particular the following:

Glycidyl ethers of monofunctional saturated or unsaturated, branched or unbranched, cyclic or open-chain $C_4$-$C_{30}$ alcohols, in particular selected from the group comprising butanol glycidyl ether, hexanol glycidyl ether, 2-ethylhexanol glycidyl ether, allyl glycidyl ether, tetrahydrofurfuryl and furfuryl glycidyl ethers, and trimethoxysilyl glycidyl ether.

Glycidyl ethers of difunctional saturated or unsaturated, branched or unbranched, cyclic or open-chain $C_2$-$C_{30}$ alcohols, in particular selected from the group comprising ethylene glycol, butanediol, hexanediol, and octanediol gylcidyl ethers, cyclohexanedimethanol digylcidyl ether, and neopentyl glycol diglycidyl ether.

Glycidyl ethers of tri- or polyfunctional, saturated or unsaturated, branched or unbranched, cyclic or open-chain alcohols such as epoxidized castor bean oil, epoxidized trimethylolpropane, epoxidized pentaerythrol, or polyglycidyl ethers of aliphatic polyols such as sorbitol, glycerin, or trimethylolpropane.

Glycidyl ethers of phenol and aniline compounds, in particular selected from the group comprising phenyl glycidyl ether, cresyl glycidyl ether, p-tert-butylphenyl glycidyl ether, nonylphenol glycidyl ether, 3-n-pentadecenyl glycidyl ether (from cashew shell oil), N,N-diglycidylaniline, and the triglycidyl [ether] of p-aminophenol.

Epoxidized amines such as N,N-diglycidylcyclohexylamine.

Epoxidized mono- or dicarboxylic acids, in particular those selected from the group comprising neodecanoic acid glycidyl esters, methacrylic acid glycidyl esters, benzoic acid glycidyl esters, phthalic acid, tetra- and hexahydrophthalic acid diglycidyl esters, and diglycidyl esters of dimeric fatty acids, and terephthalic acid and trimellitic acid gylcidyl esters.

Epoxidized di- or trifunctional, low- to high-molecular polyether polyols, in particular polyethylene glycol-diglycidyl ether or polypropylene glycol-diglycidyl ether.

Particularly preferred are hexanediol diglycidyl ether, cresyl glycidyl ether, p-tert-butylphenyl glycidyl ether, polypropylene glycol diglycidyl ether, and polyethylene glycol diglycidyl ether.

The total fraction of reactive diluent G, containing the epoxide groups, is advantageously 0.1-20% by weight, preferably 1-8% by weight, relative to the weight of the overall composition.

The composition may include further constituents, in particular catalysts, stabilizers, especially heat and/or light stabilizers, thixotropic agents, softeners, solvents, mineral or organic fillers, blowing agents, dyes and pigments, anticorrosion agents, surfactants, antifoaming agents, and bonding agents.

Particularly suited as softeners are phenol alkyl sulfonate and N-butylbenzenesulfonamide, which are commercially available from Bayer as MESAMOLL and DELLATOL BBS, respectively.

Particularly suited as stabilizers are optionally substituted phenols such as butylhydroxytoluene (BHT) or WINGSTAY T (Elikem), sterically hindered amines, or N-oxyl compounds such as TEMPO (Evonik).

The described thermosetting epoxy resin compositions after curing are characterized by high impact strength and a glass transition temperature typically greater than 100° C.

It has been shown that the described thermosetting epoxy resin compositions are particularly suited as single-component adhesives. Such a single-component adhesive has many applications. In particular, thermosetting single-component adhesives may thus be obtained which are characterized by high impact strength. Such adhesives are necessary for bonding heat-stable materials. Heat-stable materials are understood to mean materials which are dimensionally stable at a curing temperature of 100-220° C., preferably 120-200° C., at least during the curing time. These involve in particular metals, and plastics such as ABS, polyamide, and polyphenylene ether, composite materials such as SMC, GFRP unsaturated polyester, and epoxy or acrylate composites. The application in which at least one material is a metal is preferred. A particularly preferred use is the adhesive bonding of identical or different metals, in particular for body shells in the automotive industry. The preferred metals are primarily steel, in particular electrogalvanized steel, hot-dip galvanized steel, lubricated steel, Bonazinc-coated steel, and subsequently phosphated steel, as well as aluminum, in particular in the variants typically used in automobile manufacture.

Such an adhesive is in particular first contacted with the materials to be bonded, at a temperature between 10° C. and 80° C., in particular between 10° C. and 60° C., and is subsequently cured at a temperature of typically 100-220° C., preferably 120-200° C.

A further aspect of the present invention relates to a method for adhesively bonding heat-stable substrates, having the following steps:

i) Applying a thermosetting epoxy resin composition, as described in detail above, to the surface of a heat-stable substrate S1, in particular a metal;

ii) Contacting the applied thermosetting epoxy resin composition with the surface of a further heat-stable substrate S2, in particular a metal;

iii) Heating the epoxy resin composition to a temperature of 100-220° C., in particular 120-200° C., preferably 160-190° C.;

wherein substrate S2 is composed of a material which is identical to or different from substrate S1.

Substrate S2 is composed of a material. which is identical to or different from substrate S1.

A bonded article results from such a method for adhesively bonding heat-stable materials. Such an article is preferably a vehicle or a mounted part of a vehicle.

Of course, in addition to thermosetting adhesives, sealants or coatings may be realized using a composition according to the invention. Furthermore, the compositions according to the invention are suitable for other applications besides automobile manufacture. Mentioned in particular are related applications in the manufacture of transport means such as ships, trucks, buses, or rail vehicles, or in the manufacture of consumer goods such as washing machines, for example.

The materials adhesively bonded using a composition according to the invention are used at temperatures that are typically between 120° C. and −40° C., preferably between 100° C. and −40° C., in particular between 80° C. and −40° C.

It is particularly preferred to use the thermosetting epoxy resin composition according to the invention as a thermosetting adhesive for body shells in vehicle manufacture.

A further aspect of the present invention thus relates to a cured epoxy resin composition which is obtained by heating a thermosetting epoxy resin composition described in detail above.

It has been shown that compositions containing silanes of formula (I), in particular of formula (I a), allow a large reduction in the curing temperature without great impairment of their storage stability. It is thus possible to meet the desired requirements of the industry for a reduction in the curing temperature to below 180° C., even after a very short time, typically 10 to 15 minutes. It has also been shown that high glass transition temperatures of greater than 100° C. as well as increased impact strengths may be achieved, which are required in particular for use of these single-component thermosetting epoxy resin compositions as body shell adhesives for vehicle manufacture.

Furthermore, it has been shown that the silanes of formula (I) result in increased adhesion to various subsurfaces. This is the case not only in the area of epoxy adhesives or coatings, but in other areas as well.

Thus, silanes of formula (I) may also be used in general as bonding agents, for example in primers for adhesives, in particular for wet-curing single-component polyurethane adhesives.

EXAMPLES

Preparation of 1,1-dimethyl-3-(3-(trimethoxysilyl)propyl)urea 5.0 g (46.5 mmol) N,N-dimethylcarbamoyl chloride (Sigma-Aldrich, Switzerland) and 40 mL dried dioxane (Sigma-Aldrich, Switzerland) were added to a 250-mL round-bottom two-neck flask equipped with a reflux cooler. 4.71 g (46.5 mmol) triethylamine (Sigma-Aldrich, Switzerland) and 8.34 g (46.5 mmol) 3-aminopropyltrimethoxysilane (Silquest A-1110, Momentive Performance Materials Inc., USA) were added dropwise under nitrogen, with stirring. After the exothermic reaction subsided, the resulting whitish suspension was stirred at 90° C. for 3 hours. A gradual color change to orange was observed. After cooling to 50° C., the solid was separated by double filtration, and the solvent was removed at 60° C. for 1 hour on a rotary evaporator. 9.6 g of the desired silane was obtained as a brown liquid. The silane was designated as DMA1100 and used without further purification.

The infrared spectrum of DMA1100 was measured on a Perkin-Elmer 1600 FT-IR instrument (ATR measuring unit using ZnSe crystal, absorption bands expressed in wave numbers ($cm^{-1}$), measurement window: 4000-650 $cm^{-1}$):

IR ($cm^{-1}$): 3343 ν(NH), 2938 ν(CH), 2838 ν(CH), 1631 ν(CO), 1532 δ(CNH)+ν(CN), 1268 ν(CN)+δ(CNH), 1226 ν(CN)+δ(CNH), 1074 ν(SiO)+ν(SiC), 805 ν(SiO)+ν(SiC), 767 ν(SiO)+ν(SiC).

3,3'-(4-Methyl-1,3-phenylene)bis(1,1-dimethylurea) ("HSRef.1")

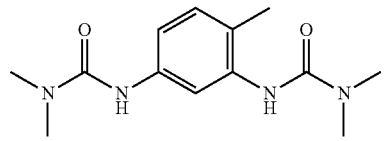

3,3'-(4-Methyl-1,3-phenylene)bis(1,1-dimethylurea) from Sigma-Aldrich, Switzerland, was used. This urea compound is not according to the invention.

Preparation of SM1 Impact Modifier 150 g poly-THF2000 (OH number 57 mg/g KOH, BASF) and 150 g Liquiflex H(OH number 46 mg/g KOH, Krahn) were dried for 30 minutes at 105° C. under vacuum. After the temperature was reduced to 90° C., 64.0 g isophorone diisocyanate (Evonik) and 0.13 g dibutyltin dilaurate were added. The reaction was carried out under vacuum at 90° C. until the NCO content was constant at 3.30% after 2.5 h (calculated NCO content: 3.38%). 103.0 g CARDOLITE NC-700 (Cardanol, Cardolite) was then added as blocking agent. Stirring of the mixture continued under vacuum at 105° C. until the NCO content had dropped below 0.1% after 3.5 h.

Preparation of Thermosetting Epoxy Resin Compositions

Comparative compositions Ref.1 and Ref.2 as well as composition 1 according to the invention as presented in Table 1 were prepared. In each case the constituents are given in parts by weight. The urea compounds DMA1100 and HSRef.1 were used in such a way that they contained the same quantities of urea groups.

Test Methods:

Tensile Shear Strength (TSS) (DIN EN 1465)

The test specimens were produced from the described example compositions, using electrogalvanized DC04 steel (eloZn) having dimensions of 100×25×0.8 mm, with an adhesive surface of 25×10 mm and a layer thickness of 0.3 mm. Curing was performed for 30 min at 175° C. The tensile speed was 10 mm/min. The value thus measured is designated as "$TSS_{175° C.}$"

To compare the underbake tolerance, tensile shear strength test specimens were also correspondingly produced and measured, wherein the curing occurred by heating for 15 minutes at 165° C. ("$TSS_{165° C.}$").

Cleavage Resistance Under Impact Loading (ISO 11343)

The test specimens were produced from the described example compositions, using electrogalvanized DC04 steel (eloZn) having dimensions of 90×20×0.8 mm, with an adhesive surface of 20×30 mm and a layer thickness of 0.3 mm. Curing was performed for 30 min at 180° C. The cleavage resistance under impact loading was measured in each case at room temperature. The impact speed was 2 m/s. The area under the measurement curve (from 25% to 90% according to ISO 11343) is given as the fracture energy (FE) in joules.

Viscosity

The adhesive samples were measured on a Bohlin CVO 120 viscosimeter, plate/plate (diameter 25 mm, gap width 1 mm), frequency 5 Hz, 0.01 deflection, temperature 23-53° C., 10° C./min. The viscosity was determined from the measured curve as complex viscosity at 25° C.

Storage Stability

An expedited procedure at elevated temperature was used for determining the storage stability at room temperature. The viscosity of the compositions at room temperature was measured immediately after production ("$\eta_0$") and compared to the value at room temperature after storage in a tightly sealed container for 7 days at 60° C. ("$\eta_A$"). The value $\Delta\eta$ according to formula $(\eta_A/\eta_0)-1$ was determined as the apparent measure of the storage stability.

Glass Transition Temperature ($T_g$)

The glass transition temperature was determined by DSC using a Mettler DSC822$^e$ instrument. In each case 10-20 mg of the compositions were weighed into an aluminum crucible. After the sample had cured in the DSC for 30 min at 175° C., it was cooled to −20° C. and then heated to 150° C. at a heating rate of 10° C./min. The glass transition temperature was determined as the inflection point from the measured DSC curve, using DSC software.

Curing Characteristics

DSC was performed on a Mettler DSC 822$^E$ instrument for each of the epoxy resin compositions mixed in this manner (heating from 25° C. to 250° C., with a heating rate of 10 K/minute). The measured curve was used to determine the maximum of the reaction peak as $T_{Peak\text{-}DSC}$ as well as the onset $T_{Onset\text{-}DSC}$ calculated from the curve.

TABLE 1

Compositions and results.

|  | Ref1 | Ref2 | 1 |
|---|---|---|---|
| D.E.R. 331 (Dow) Bisphenol-A diglycidyl ether, liquid epoxy resin | 40.0 | 40.0 | 40.0 |
| Polypox R7 (UPPC) tert-Butylphenyl glycidyl ether | 3.0 | 3.0 | 3.0 |
| POLYDIS 3614 (Struktol) Epoxy resin-modified acrylonitrile/butadiene copolymer (CTBN) | 15.0 | 15.0 | 15.0 |
| SM1 | 15.0 | 15.0 | 15.0 |
| HSRef, 1 |  | 0.51 |  |
| DMA1100 |  |  | 0.97 |
| Dicyandiamide (Degussa) | 4.0 | 4.0 | 4.0 |
| Filler mixture | 19.0 | 19.0 | 19.0 |
| TSS$_{175°\,C.}$ [MPa] | 21.4 | 21.7 | 18.7 |
| TSS$_{165°\,C.}$ [MPa] | 0.0* | 20.1 | 18.4 |
| FE$^1$ at 23° C. [J] | 14.2 | 16.1 | 10.7 |
| $\eta_0$ [mPas] | 395 | 350 | 412 |
| $\eta_A$ [mPas] | 395 | 1340 | 517 |
| $\Delta\eta$ [%] | 0 | 283 | 25 |
| $T_g$ [° C.] | 106 | 105 | 104 |
| $T_{Onset\text{-}DSC}$ [° C.] | 189 | 172 | 168 |
| $T_{Peak\text{-}DSC}$ [° C.] | 198 | 181 | 178 |

$^1$FE = fracture energy.
*Adhesive did not cure.

The results from Table 1 show that Comparative Example Ref1 has essentially the same storage stability as for Example 1, but in contrast to Example 1 did not cure at lower curing temperatures (165° C., 15 min). Comparative Example Ref2 shows that curing at lower temperatures is possible using the aromatic urea HSRef.1, but such a composition is not stable under storage. On the other hand, Example 1 is stable under storage and is also curable at lower temperatures. The curing at lower temperatures is also apparent from the lower DSC values ($T_{Peak\text{-}DSC}$ and $T_{Onset\text{-}DSC}$).

In addition, the values from Table 1 show that in addition to a high glass transition temperature and high impact strength, Example 1 has good mechanical properties which are very well suited for use as body shell adhesive for vehicle manufacture.

The invention claimed is:

1. A thermosetting epoxy resin composition comprising:
   at least one epoxy resin EH having, on average, more than one epoxide group per molecule; and
   at least one silane of formula (I);

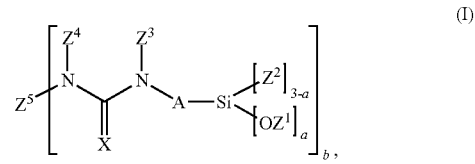

wherein A is an optionally branched alkylene group containing 1 to 4 C atoms, or a phenylene group;
wherein $Z^1$ is H or an alkyl group containing 1 to 4 C atoms;
wherein $Z^2$ is H, a phenyl group, or an alkyl group containing 1 to 8 C atoms;
wherein $Z^3$ is:
   H,
   a monofunctional aromatic or cycloaliphatic or aliphatic group containing 1 to 8 C atoms, which optionally contains at least one carboxylate, nitrile, nitro, phosphonate, or sulfonic or sulfonate group, or
   a group having a formula of A-Si($Z^2$)$_{3-a}$(OZ$^1$)$_a$;
wherein $Z^4$ is H or a monofunctional aromatic or cycloaliphatic or aliphatic group containing 1 to 8 C atoms;
wherein $Z^5$ is:
   a bi-functional aromatic or araliphatic or cycloaliphatic or aliphatic group containing 1 to 40 C atoms, or
   a group having a formula of A-Si($Z^2$)$_{3-a}$(OZ$^1$)$_a$;
wherein X is O or S;
wherein a is 1 or 2 or 3; and
wherein b is 1 or 2 or 3 or 4;
with the proviso that either $Z^3$ or $Z^4$ is H.

2. The thermosetting epoxy resin composition of claim 1, wherein the silane of formula (I) is present on the surface of an inorganic filler.

3. The thermosetting epoxy resin composition of claim 2, wherein the inorganic filler contains at least one metal atom selected from the group consisting of Ca atoms, Si atoms, Al atoms, and mixtures thereof.

4. The thermosetting epoxy resin composition of claim 3, wherein the silane of formula (I) is coated onto the surface of the inorganic filler.

5. The thermosetting epoxy resin composition of claim 3, wherein the silane of formula (I) is chemically bound with the inorganic filler.

6. The thermosetting epoxy resin composition of claim 1, wherein the silane of formula (I) is present in the thermosetting epoxy resin composition in amount of from 0.001-20% by weight, relative to the weight of the thermosetting epoxy resin composition.

7. The thermosetting epoxy resin composition of claim 1, further comprising at least one heat-activatable curing agent B selected from the group consisting of dicyandiamide, guanamine, guanidine, aminoguanidine, a substituted urea, a phenyldimethyl urea, imidazoles, imidazole salts, imidazolines, amine complexes and derivatives thereof.

8. The thermosetting epoxy resin composition of claim 1, wherein the thermosetting epoxy resin composition further comprises at least one impact modifier D.

9. The thermosetting epoxy resin composition of claim 8, wherein the impact modifier D is selected from the group consisting of blocked polyurethane polymers, liquid rubbers, epoxy resin-modified liquid rubbers, block copolymers, and core-shell polymers.

10. The thermosetting epoxy resin composition of claim 9, wherein the impact modifier D is a blocked polyurethane polymer of formula (IV)

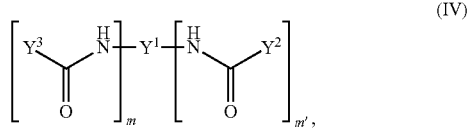

(IV)

wherein:
  $Y^1$ is a linear or branched polyurethane polymer PU1, terminated by m+m' isocyanate groups, after removal of all end-position isocyanate groups;
  $Y^2$ is independently a blocking group that cleaves at a temperature above 100° C.;
  $Y^3$ is independently a group of formula (IV')

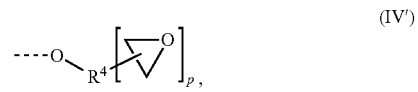

(IV')

wherein $R^4$ is a radical of an aliphatic, cycloaliphatic, aromatic, or araliphatic epoxy, containing a primary or secondary hydroxyl group, after removal of the hydroxide and epoxy groups;
  wherein p is 1, 2, or 3, and
  wherein m and m' each stand for an integer between 0 and 8, with the proviso that a value of m+m' is from 1 to 8.

11. A method for the adhesive bonding of heat-stable substrates, the method comprising:
  i) applying the thermosetting epoxy resin composition of claim 1 to a surface of a first heat-stable substrate S1;
  ii) contacting the applied thermosetting epoxy resin composition with the surface of second heat-stable substrate S2; and
  iii) heating the contacted thermosetting epoxy resin composition to a temperature of 100-220° C.;
  wherein substrate S2 is composed of a material that is identical to or different from substrate S1.

12. A cured epoxy resin composition obtained by heating the thermosetting epoxy resin composition claim 1.

* * * * *